(12) United States Patent
Pattikonda et al.

(10) Patent No.: US 11,526,034 B1
(45) Date of Patent: Dec. 13, 2022

(54) EYEWEAR WITH FLEXIBLE AUDIO AND ADVANCED FUNCTIONS

(71) Applicants: Ram Pattikonda, Plano, TX (US); Shariq Hamid, Plano, TX (US)

(72) Inventors: Ram Pattikonda, Plano, TX (US); Shariq Hamid, Plano, TX (US)

(*) Notice: Subject to any disclaimer, the term of this patent is extended or adjusted under 35 U.S.C. 154(b) by 330 days.

(21) Appl. No.: 16/584,884

(22) Filed: Sep. 26, 2019

Related U.S. Application Data

(63) Continuation-in-part of application No. 16/572,661, filed on Sep. 17, 2019, now Pat. No. 11,385,481, which is a continuation-in-part of application No. 15/884,823, filed on Jan. 31, 2018, now Pat. No. 10,423,009.

(60) Provisional application No. 62/856,219, filed on Jun. 3, 2019, provisional application No. 62/845,334, filed on May 9, 2019, provisional application No. 62/807,864, filed on Feb. 20, 2019, provisional application No. 62/788,446, filed on Jan. 4, 2019, provisional application No. 62/733,577, filed on Sep. 19, 2018, provisional application No. 62/453,108, filed on Feb. 1, 2017.

(51) Int. Cl.
| | |
|---|---|
| G02C 11/00 | (2006.01) |
| H04R 1/02 | (2006.01) |
| H02J 7/02 | (2016.01) |
| A61B 5/024 | (2006.01) |
| G06F 3/01 | (2006.01) |
| H04R 1/34 | (2006.01) |

(52) U.S. Cl.
CPC .......... *G02C 11/10* (2013.01); *A61B 5/02438* (2013.01); *G06F 3/012* (2013.01); *H02J 7/025* (2013.01); *H04R 1/028* (2013.01); *H04R 1/345* (2013.01)

(58) Field of Classification Search
CPC ..... G02C 11/10; G06F 3/012; A61B 5/02438; H04R 1/028; H04R 1/345; H02J 7/025
USPC .................................................. 351/41, 158
See application file for complete search history.

(56) References Cited

U.S. PATENT DOCUMENTS

| | | | |
|---|---|---|---|
| 4,663,495 A | 5/1987 | Berman et al. | |
| 5,805,267 A * | 9/1998 | Goldman | A61N 5/0618 351/203 |
| 7,651,220 B1 | 1/2010 | Pattikonda | |
| 7,970,172 B1 * | 6/2011 | Hendrickson | G02C 7/101 382/103 |
| 8,783,861 B2 * | 7/2014 | Blum | G02C 11/10 351/113 |
| 9,025,016 B2 * | 5/2015 | Wexler | G06K 9/325 348/62 |
| 9,122,083 B2 * | 9/2015 | Blum | G02C 11/04 |
| 9,720,259 B2 * | 8/2017 | Hart | G02C 11/10 |
| 9,910,298 B1 * | 3/2018 | Sales | G02C 11/04 |
| 9,980,054 B2 * | 5/2018 | McCracken | G02C 11/10 |
| 10,453,264 B1 * | 10/2019 | Hogue | G06T 19/006 |
| 2012/0105740 A1 * | 5/2012 | Jannard | H04M 1/6066 348/794 |

(Continued)

*Primary Examiner* — Tuyen Tra
(74) *Attorney, Agent, or Firm* — Michael Diaz

(57) ABSTRACT

Eyewear providing flexible audio to a user. The eyewear includes a frame having two temple arms. The frame also has a front rim retaining two lenses. The eyewear also includes an open ear speaker for firing directional audio to an ear of a user, thereby providing semi-private audio to the user. The eyewear may include a wireless connection to another smart device or network.

26 Claims, 15 Drawing Sheets

(56) References Cited

U.S. PATENT DOCUMENTS

| | | | |
|---|---|---|---|
| 2013/0329183 A1* | 12/2013 | Blum | G06F 3/011 |
| | | | 351/158 |
| 2014/0130864 A1 | 5/2014 | Lunt et al. | |
| 2014/0268008 A1* | 9/2014 | Howell | G02C 11/10 |
| | | | 351/158 |
| 2014/0268016 A1* | 9/2014 | Chow | H04R 1/028 |
| | | | 351/158 |
| 2017/0246070 A1* | 8/2017 | Osterhout | H04N 5/23296 |
| 2018/0131847 A1* | 5/2018 | Kokonaski | H04N 5/23293 |
| 2020/0218094 A1* | 7/2020 | Howell | G02C 11/06 |
| 2020/0292843 A1* | 9/2020 | Villalpando | G02C 11/10 |

* cited by examiner

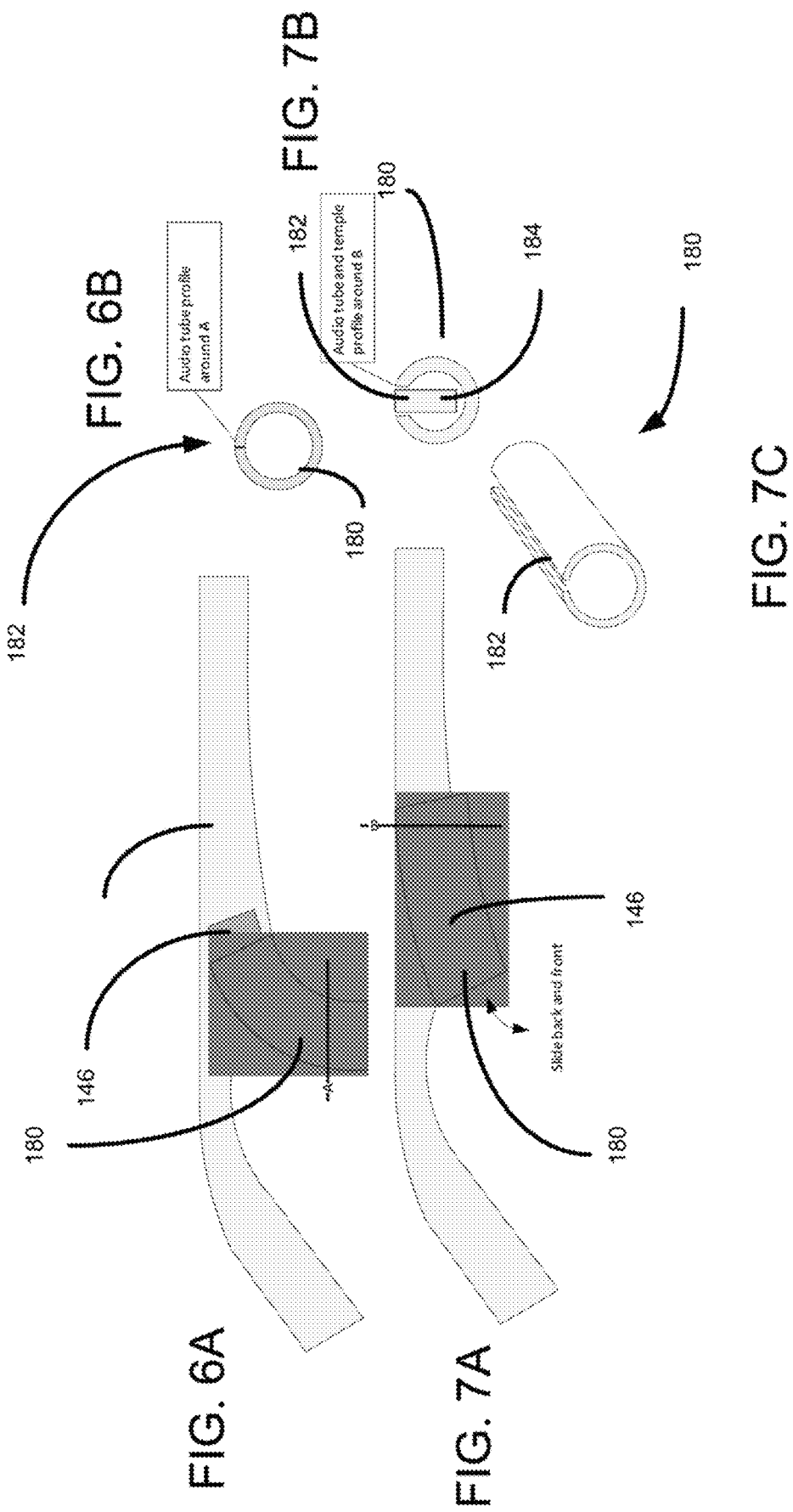

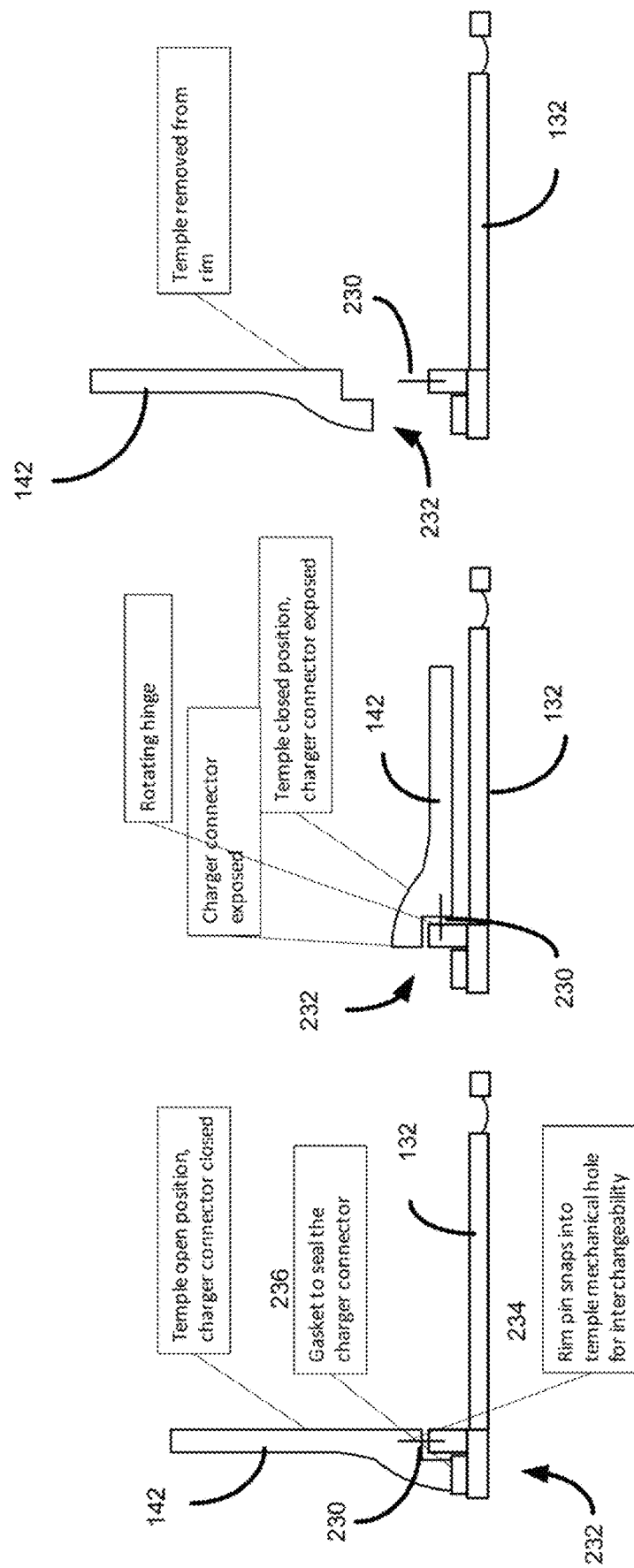

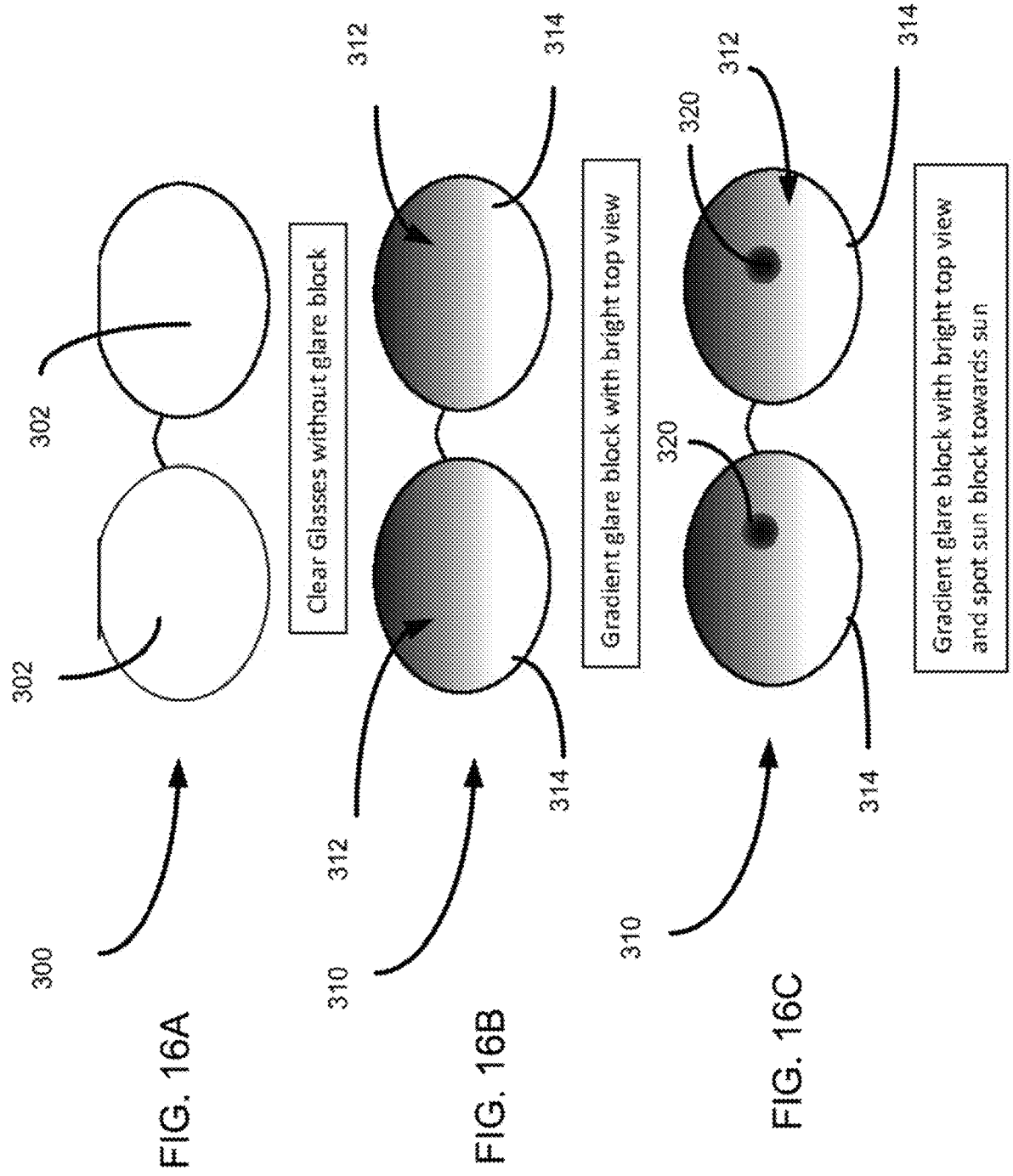

EYEWEAR WITH FLEXIBLE AUDIO AND ADVANCED FUNCTIONS

RELATED APPLICATIONS

This utility application is a continuation-in-part of U.S. patent application Ser. No. 16/572,661 filed on Sep. 17, 2019 which is a continuation-in-part of U.S. patent application Ser. No. 15/884,823 filed on Jan. 31, 2018 by Ram Pattikonda, Shariq Hamid, and which claims the benefits of U.S. Provisional Patent Application Serial No. claims the benefit of U.S. Provisional Patent Application Ser. No. 62/453,108 by Ram Pattikonda and Shariq Hamid filed Feb. 1, 2017 is hereby incorporated by reference. Additionally, this utility application is a continuation-in-part of U.S. patent application Ser. No. 15/857,679 filed on Dec. 29, 2017 and is hereby incorporated by reference. In addition, this application claims the benefit of U.S. Provisional Patent Application Ser. No. 62/733,577 by Ram Pattikonda and Shariq Hamid filed Sep. 19, 2018 is hereby incorporated by reference. Additionally, this application claims the benefit of U.S. Provisional Patent Application Ser. No. 62/788,446 by Ram Pattikonda and Shariq Hamid filed Jan. 4, 2019 is hereby incorporated by reference. In addition, this application claims the benefit of U.S. Provisional Patent Application Ser. No. 62/807,864 by Ram Pattikonda and Shariq Hamid filed Feb. 20, 2019 is hereby incorporated by reference. Additionally, this application claims the benefit of U.S. Provisional Patent Application Ser. No. 62/856,219 by Ram Pattikonda and Shariq Hamid filed Jun. 3, 2019 is hereby incorporated by reference. In addition, this application claims the benefit of U.S. Provisional Application Ser. No. 62/845,334 by Ram Pattikonda and Shariq Hamid filed May 9, 2019 is hereby incorporated by reference.

BACKGROUND OF THE INVENTION

Field of the Invention

This invention relates to wearable eyewear. Specifically, and not by way of limitation, the present invention relates to wearable eyewear providing audio and other functionalities.

Description of the Related Art

Smart wearable devices, such as smartwatches, fitness bands or smart glasses provide fitness information and access to connected mobile phones. They collect fitness information, such as steps walked, quality of sleep and the user's heart rate. They also connect to the user's mobile phone to provide notifications. Additionally, they also allow remote control of the phone for functions such as music or phone calls. While wrist worn smart wearables have become pervasive, the eye worn smart glasses are still not popular due to their bulk, lack of functionality and ease of use.

Eyewear devices are needed that provide audio from connected phones or from the cloud to the user in a slim form factor using directional open ear audio. It would be advantageous to have a feature providing audio fired from frame temples to the ear for a semi-private experience. While the basic function provides phone call, music and voice commands, additional features such as step counter, heartrate and should be provided in the eyewear. While providing display on see-through glass to achieve augmented reality is the best solution for smart glasses to provide phone or cloud information, they are not practical due to size, complexity and cost of such devices, They cannot provide slim good-looking solution for the user. Additionally, it would be advantageous to provide phone or cloud information to the user via audio using open directional speakers by playing audio directly or with text to speech converted audio. It is an object of the present invention to provide such an apparatus.

SUMMARY OF THE INVENTION

In one aspect, the present invention is directed to eyewear providing flexible audio to a user. The eyewear includes a frame having two temple arms. The frame also has a front rim retaining two lenses. The eyewear also includes an open ear speaker for firing directional audio to an ear of the user, thereby providing semi-private audio to the user. The eyewear may include a wireless connection to another smart device or network.

BRIEF DESCRIPTION OF THE DRAWINGS

FIG. 6A illustrates a side view of the eyewear with a sliding foam tube attached to the temple arm in an extended position;

FIG. 6B is a cross section view of the sliding foam tube;

FIG. 7A illustrates a side of the sliding foam tube in a retracted position;

FIG. 7B illustrates a cross section view of the sliding foam tube of FIG. 7A;

FIG. 70 is a front perspective view of the foam tube;

FIG. 14A is a top view of the temple arm in an open configuration with the front rim of the eyewear;

FIG. 14B is a front view of the temple arm in a closed configuration relative to the front rim of the eyewear;

FIG. 14C is a top view of the temple arm disconnected from the front rim of the eyewear;

FIG. 16A illustrates a front view of glasses having clear lenses;

FIG. 16B illustrates a front view of glasses utilizing gradient block on the lenses; and FIG. 16C is a front view the glasses of FIG. 16B using spot sun block to block glare from the sun.

DESCRIPTION OF THE INVENTION

Figure 1:
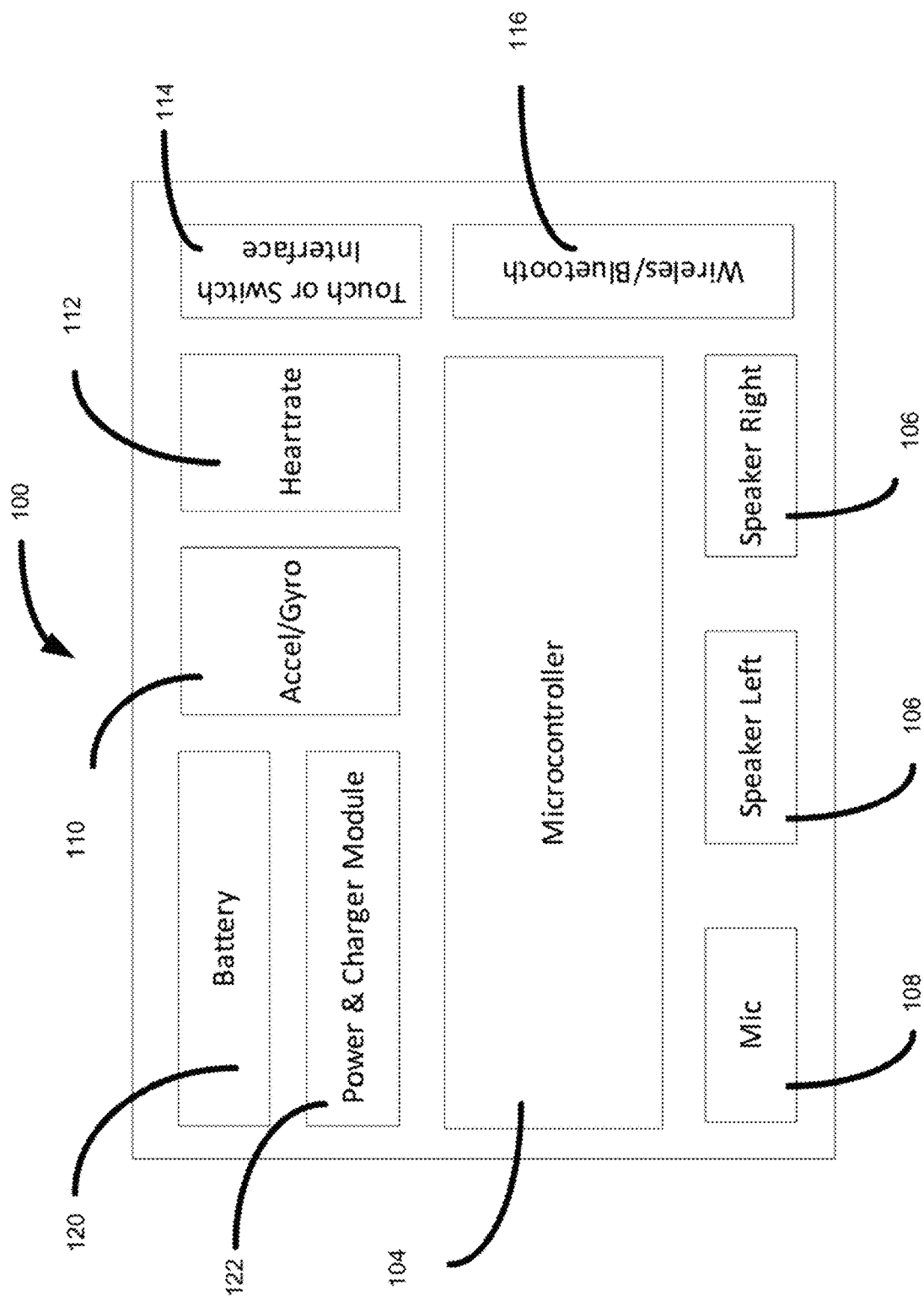
FIG. 1 is a simplified block diagram of the key components of a system utilized for wearable eyewear in one embodiment of the present invention.

The present invention is wearable eyewear providing flexible audio and other advanced functionalities. FIG. 1 is a simplified block diagram of the key components of a system 100 utilized for wearable eyewear 102 in one embodiment of the present invention. The system 100 includes a primarily microcontroller 104, stereo speakers (speakers 106), a microphone (mic) 108, and sensors, such as an accelerometer 110 and heartrate sensor 112 as well as other optional sensors for step counting, etc. The microcontroller provides the computations and brains of the system 100 with an interface to the sensors 110 and 112, speakers 106, microphone 108, touch interface 114 and wireless/Bluetooth connection module 116. In addition, the system 100 includes a battery 120 connected to a power and charger module 122 which supplies power to the microcontroller 104 and its peripherals. The accelerometer (with optional gyroscope) 110 provides motion data for step counting and detection of gestures. The heartrate sensor 112 provides heartrate and breathing measurements from the earlobe or forehead temples of the user. The touch interface 114 (or alternative button interface) provides the user control to the wearable eyewear 102. The microphone 108 also provide speech input and call functionality. Optionally, a camera (not shown) also provides input and image capture functionality. The wireless interface such as the Bluetooth or Wifi connections 116 provide data connection to a connected phone or to the cloud.

Figure 2:
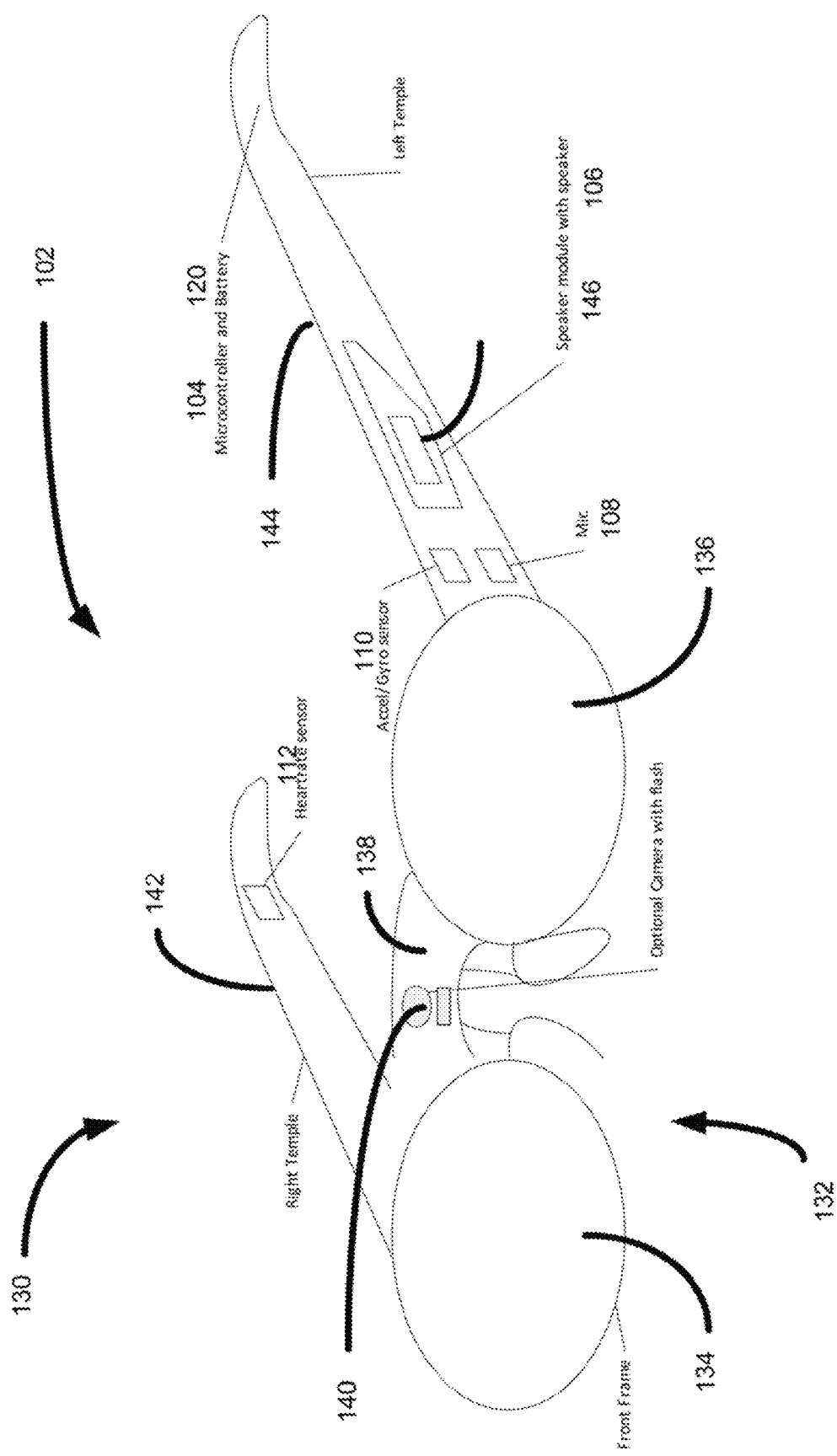
FIG. 2 is a front perspective view of the eyewear embodied as eyeglass frames.

FIG. 2 is a front perspective view of the eyewear 102 embodied as eyeglass frames 130. The eyeglass frames 130 includes a front rim 132 holding lenses 134 and 136, a nose bridge 136 having an optional camera 140, temple arms 142 and 144, and a speaker module 146 having one or more speakers 106. The speakers 106 are preferably positioned on both temple arms 142 and 144 for stereo sound. These two temple arms are either connected with wires or wireless between them. When used wirelessly, both temples need their own batteries and charging. The user may place the frames on a charging dock where the dock mates with a charging pads on both temples to charge both batteries. By using a wireless approach, the temple arms may be made swappable with different frame fronts.

Figure 3:
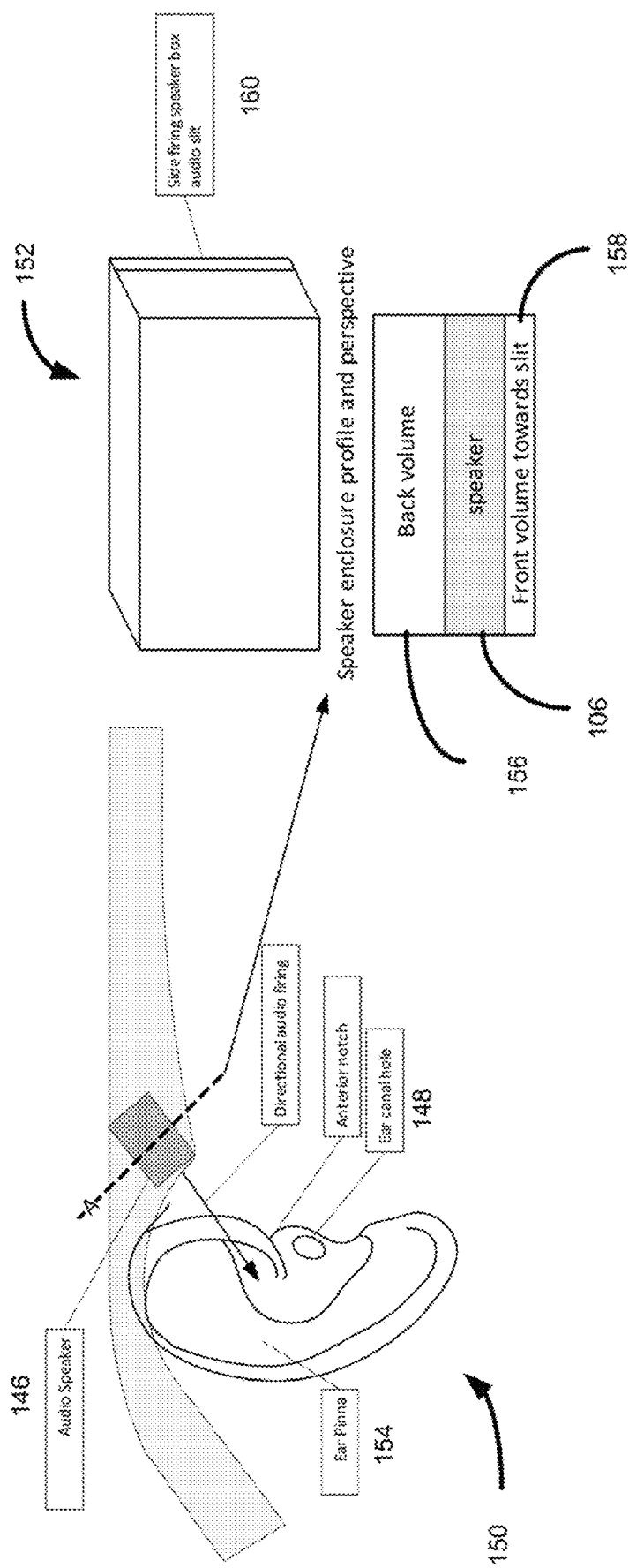
FIG. 3 is a side view of the temple arm illustrating an enlarged view of the speaker module.

FIG. 3 is a side view of the temple arm 142 illustrating an enlarged view of the speaker module 146. The speaker module 146 includes speakers 106 in a slim form which are positioned on the temple arms 142 and 144, close to the user's ear 150, firing audio directly towards the ear. The speaker module 146 is designed with a side firing enclosure 152 with audio directed towards the pinna 154 of the user's ear taking advantage of the gap near the anterior notch of the ear. This design fires the audio fully towards the pinna of the ear which acts as an amplifier. The human ear pinna is designed to amplify the audio and direct towards the ear canal hole. The normal audio waves are omnidirectional spreading in all directions. The speaker enclosure 152 is designed with suitable back volume 156, front volume 158 and an audio slit 160 for side firing and to give directivity to the audio. With this directional audio, proximity to ear and orientation towards the pinna, most of the audio will reach the ear providing a semi-private audio experience to the user. The audio enclosure and temple are designed for minimum external audio leak.

Figure 4:
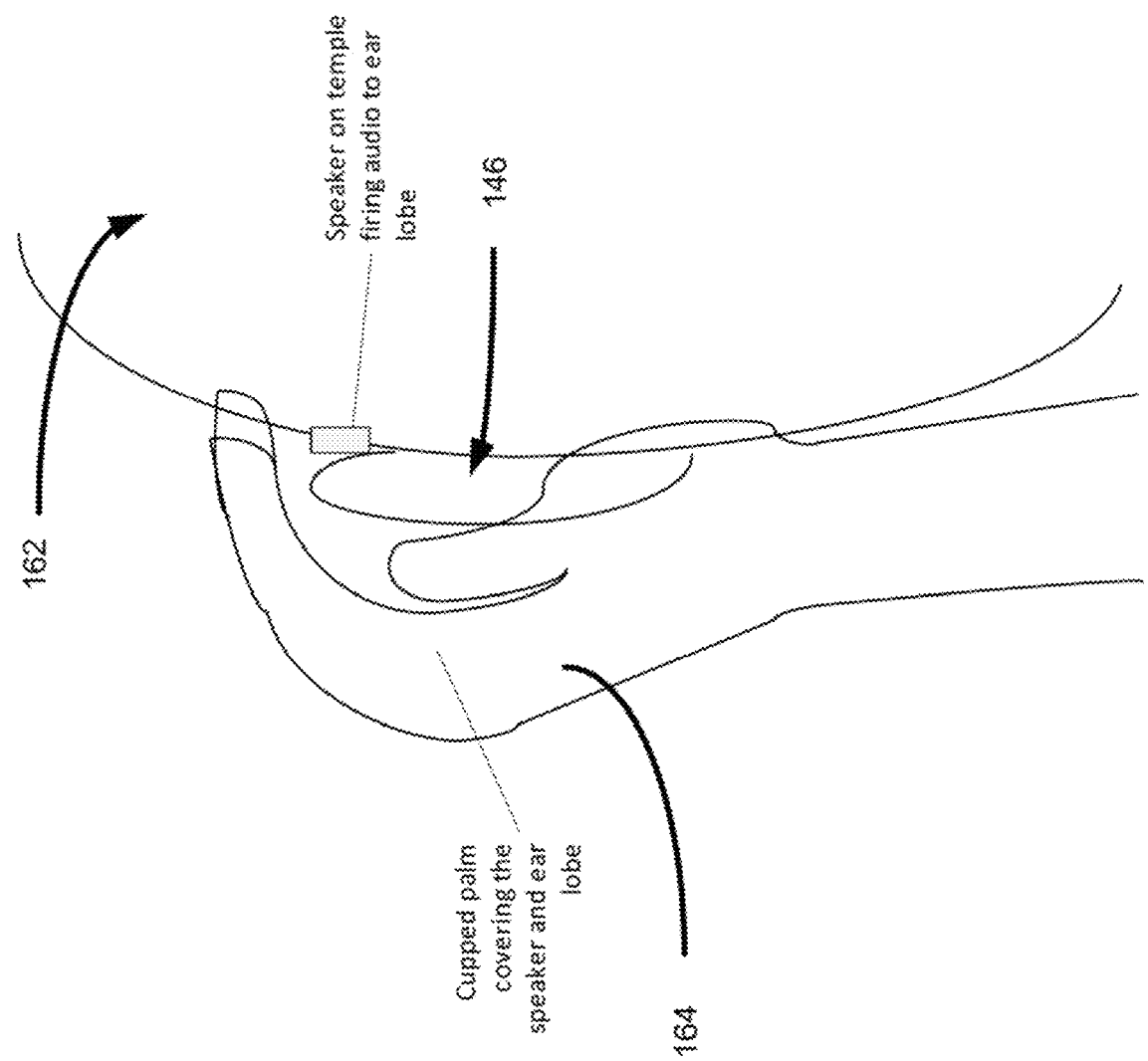
FIG. 4 is a side view of a user using a palm to provide a private audio mode.

FIG. 4 is a side view of a user 162 using a palm 164 to provide a private audio mode. The speaker audio exit position is designed such that the user may hold the palm 164 closed on the ear to get private mode audio. The audio from speaker enclosure slit is contained in palm and user's ear to provide a full private audio experience. Providing fully private audio in eyewear frame while maintaining a slim look of the frames is challenging as the frame temples do not reach the ear-canal. While the bone-conduction speakers try to solve this problem, they have many disadvantages including poor response to audio frequencies and secondary audio emissions from the bone vibrations. The present invention provides novel ways of achieving private audio to the user.

Figure 5:
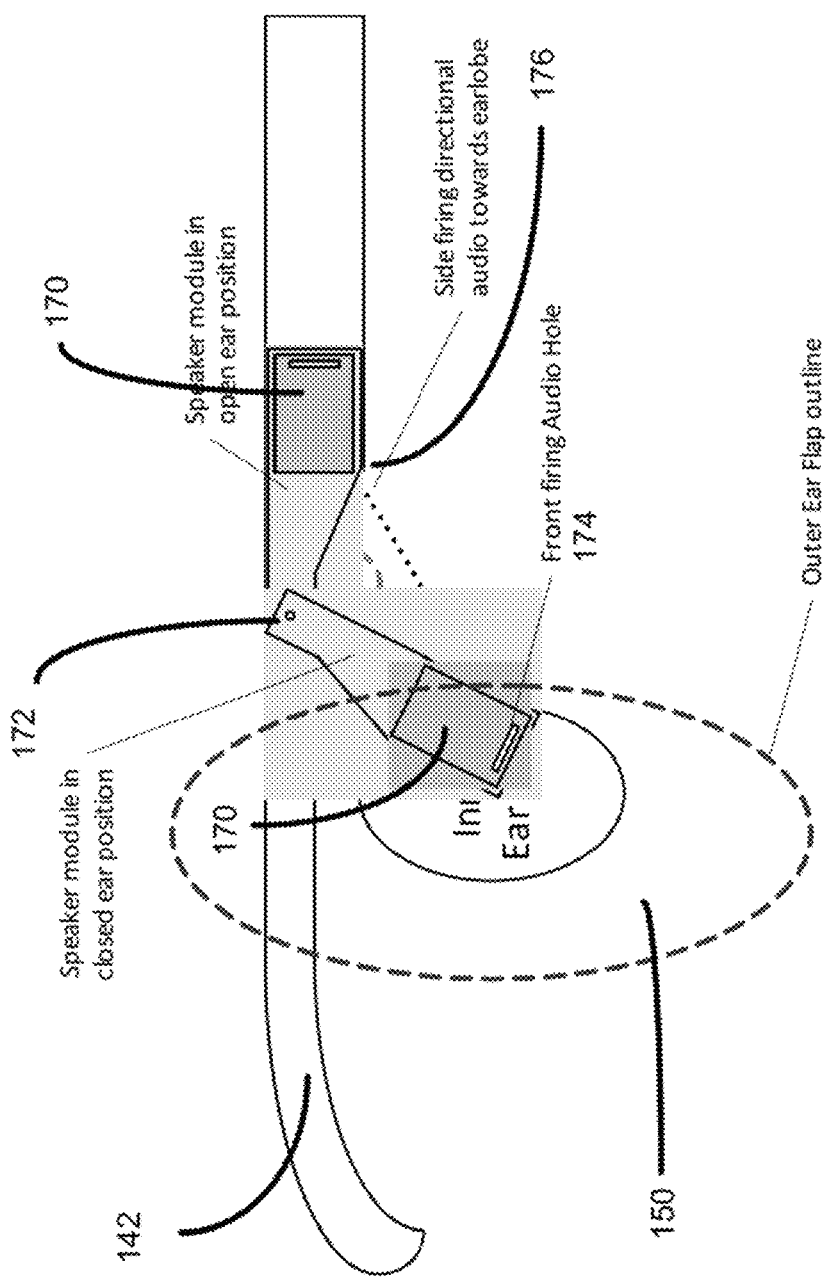
FIG. 5 is a side view of a two position speaker configuration in one embodiment of the present invention.

FIG. 5 is a side view of a two-position speaker configuration in one embodiment of the present invention. In this embodiment, an open ear speaker enclosure 170 is positioned around a rotating hinge 172. The speaker enclosure 170 may be rotated towards the ear 150 to get full private audio. This mode would deliver audio akin to a user wearing a headset. In this rotated position, a sensor would detect the module position change and change to audio parameters to suit the private audio. The volume may automatically be reduced, and frequency response changed to suit the speaker firing directly on the ear. When the speaker enclosure 170 is parked in the temple arm 142, the speaker front opening 174 may be sealed and fires from a side opening slit 176 towards the ear. When the speaker enclosure 170 is rotated down to the ear, it will fire directly into the ear in the front opening. Additional ear cushions may be provided to seal the speaker around the ear.

In another embodiment of the present invention, foam or bellow type retractable audio tubes may be used to provide a privacy mode. The audio output of the open ear speaker may be channeled directly to the ear canal hole using movable channel tubes. This tube can be made of flexible and insulating material such as NBR foam (nitrile rubber), Ethylene-vinyl acetate (EVA) foam or insulated bellow. This may be constructed to cover the typical gap of 1.3" between the audio exit slit of speaker and the user's ear canal hole and prevents audio leak in this length. Appealing design is provided by parking the channel tube on the temple when not in use. The user would retract it down only when private audio is needed. In the parked mode, the user can listen to audio in a semi-private open ear mode. Various specific materials, such as NBR foam, that bend easily for parking and fit around the ear when retracted down may be used. The material also must provide audio insulation with no leakage. The temple may have proximity detection electronics to detect the retracted position of the tube and automatically adjust the audio level to the user.

FIG. 6A illustrates a side view of the eyewear with a sliding foam tube 180 attached to the temple arm 142 in an extended position. FIG. 6B is a cross section view of the sliding foam tube 180. FIG. 7A illustrates a side of the sliding foam tube 180 in a retracted position. FIG. 7B illustrates a cross section view of the sliding foam tube 180 of FIG. 7A. In this embodiment, the tube 180 includes a slit 182. This slit 182 allows the tube to be snapped around the temple arm 142 as illustrated in FIG. 7B. FIG. 7C is a front perspective view of the foam tube 180. The temple arm may include guides 184 for the slit tube to slide into. The user may slide the tube all the way around the temple arm to the retracted or parked position. When a private audio mode is needed, the user may slide the tube down towards the ear. In the extended position down, the tube may include wire reinforcements to press against ear to seal the audio sound.

Figure 8:
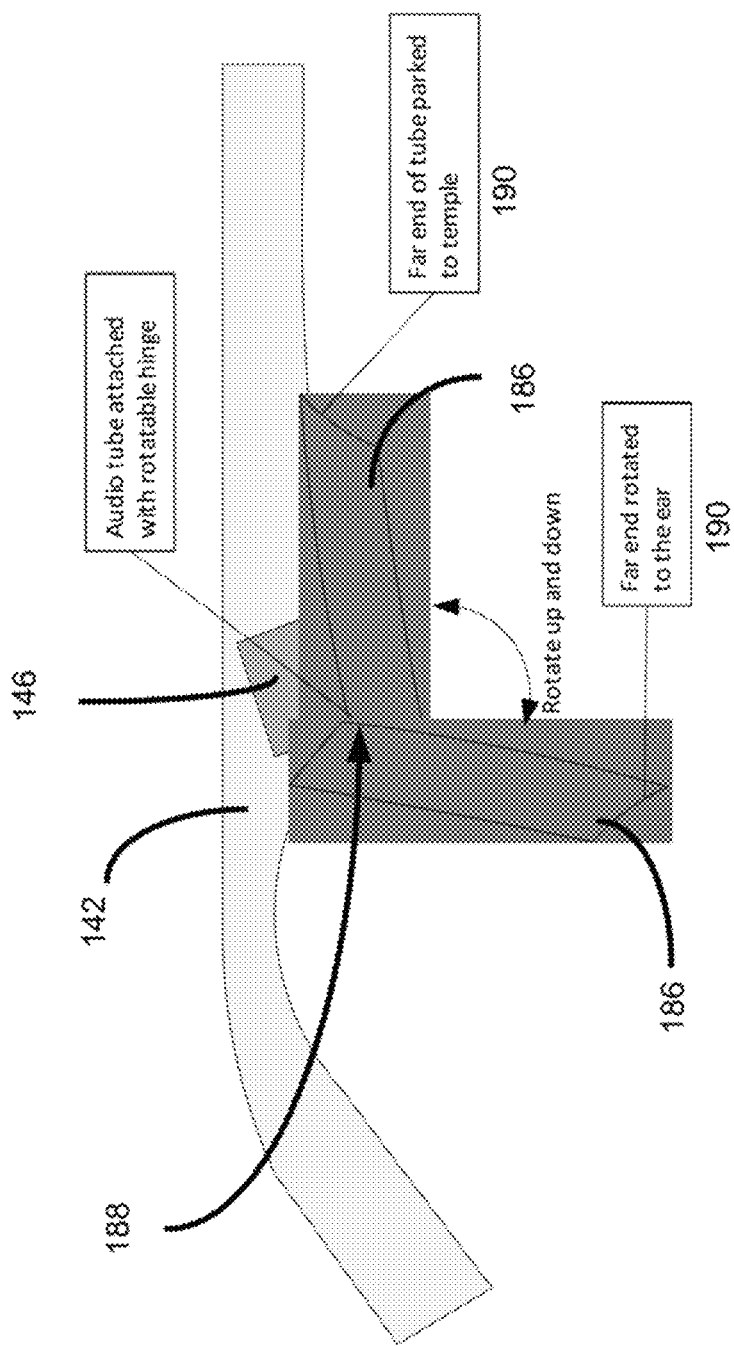
FIG. 8 is a side view of a rotating foam tube in another embodiment of the present invention.

FIG. 8 is a side view of a rotating foam tube 186 in another embodiment of the present invention. The foam tube 186 is preferably constructed without a slit and is attached parallel to the temple. The foam tube 186 is attached at a hinge point 188 where it can be rotated around the hinge. A far end 190 of the tube is either parked up to the temple or rotated down towards the ear. It is preferably held in a parked position with a mechanical snap or magnet. When the foam tube is rotated down position, it is held in the ear cup with wire reinforcements to press against ear to seal the audio sound.

Figure 9:
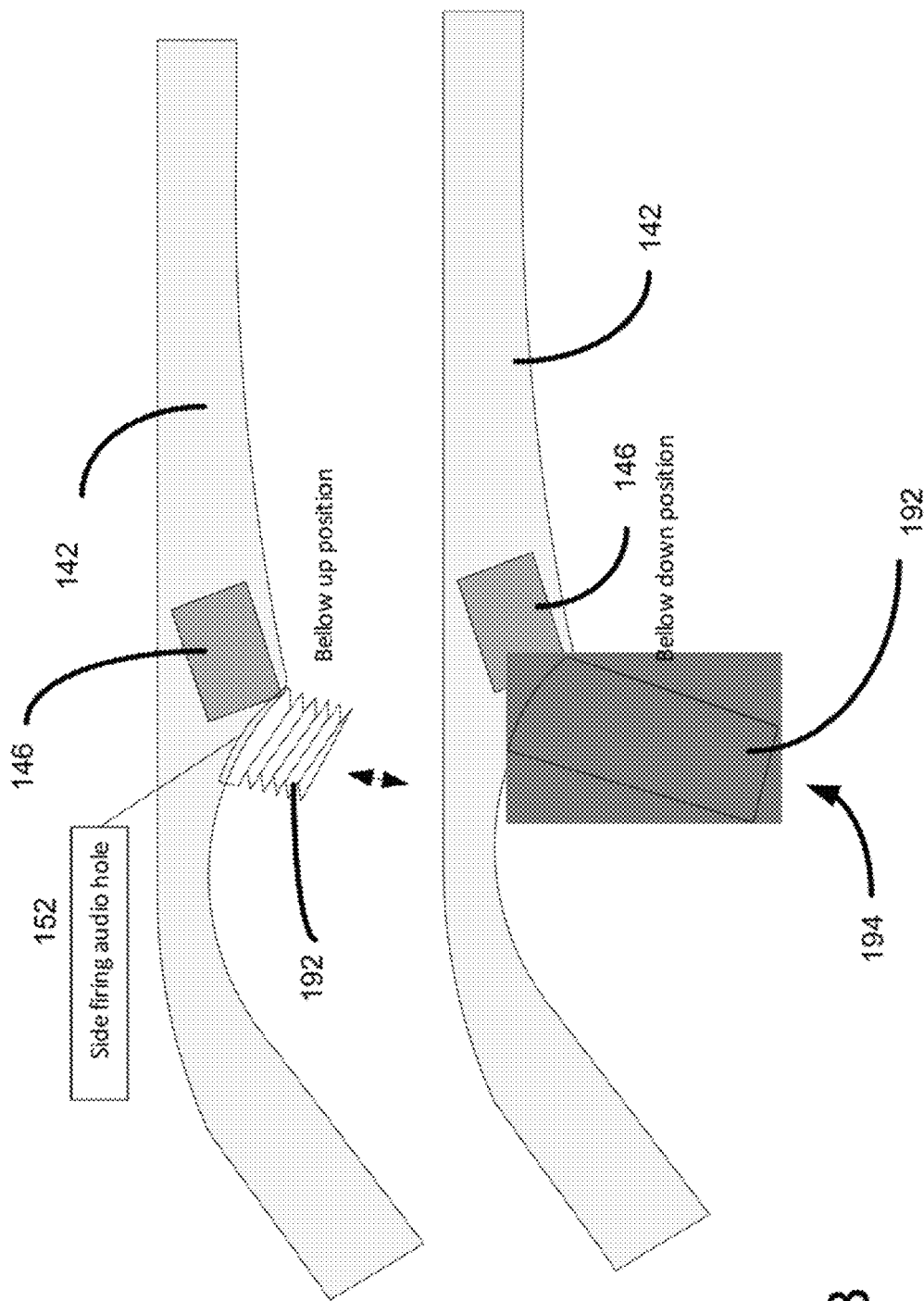
FIG. 9A is a side view of a bellow tube in an up position in another embodiment of the present invention.
FIG. 9B is a side view of the bellow tube of FIG. 9A in the down position.

FIG. 9A is a side view of a bellow tube 192 in an up position in another embodiment of the present invention. FIG. 9B is a side view of the bellow tube 192 of FIG. 9A in the down position. In this embodiment, the bellow tube is attached to the audio hole of the side fire enclosure 152. The user pulls down the bellow tube 192 and snaps a bottom end 194 into the ear cavity. When not needed, the bellow tube is pushed up where it snaps to a temple arm base with a mechanical or magnetic snap. The bellow material is utilized to provide good audio insulation.

Figure 10:
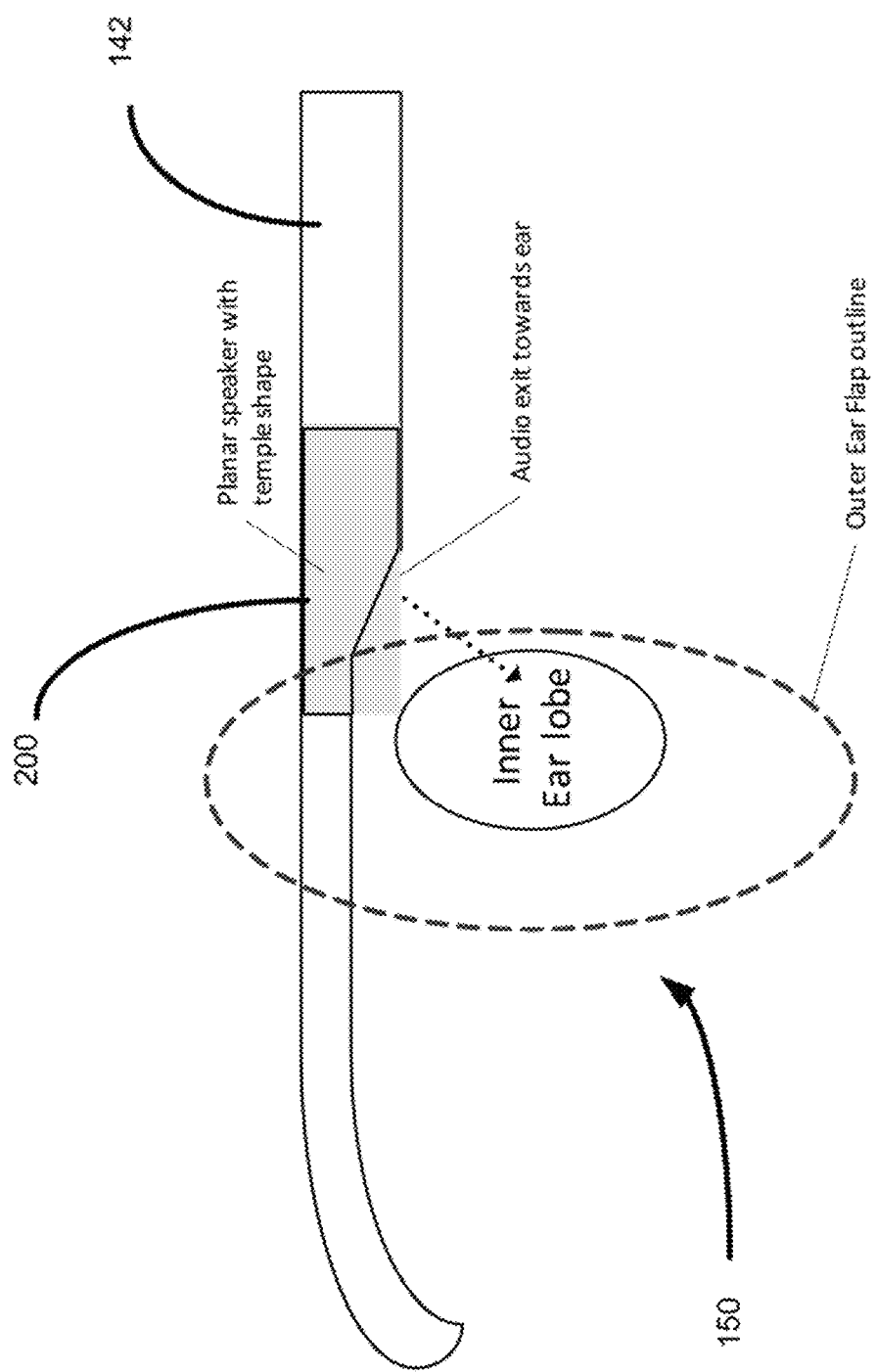
FIG. 10 is a side view of a planar speaker in another embodiment of the present invention.

FIG. 10 is a side view of a planar speaker 200 in another embodiment of the present invention. Electrostatic and planar magnetic speakers support shaped diaphragm unlike the cone speakers which use round diaphragm. This odd shape of membrane is ideally suited to be embedded in the eyewear temple arms 142 and 144. Planar magnetic speakers 200 have metal ribbon suspended between two magnetic panels. The shape of the speaker membrane can be matched to the shape of the temple arms. With the larger area of the temple they provide larger displacement, thus higher efficient sound, than cone speakers in the eyeglass temple layout. The audio exits out a bottom portion of the planar speaker 200 toward the user's ear 150.

Figure 11:
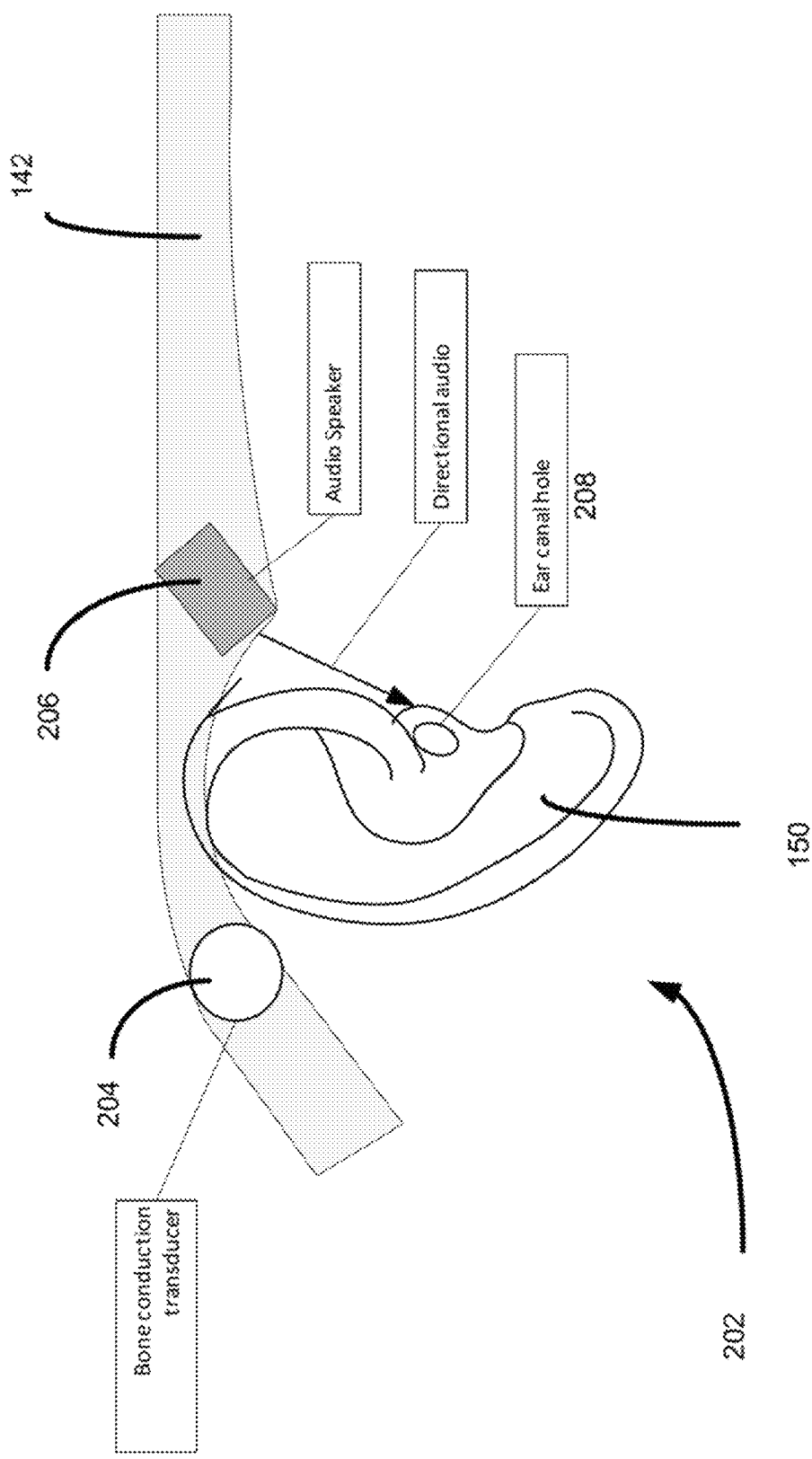
FIG. 11 is a side view of a side view of a hybrid speaker system using a bone conduction transducer and an audio speaker in another embodiment of the present invention.

FIG. 11 is a side view of a side view of a hybrid speaker system 202 using a bone conduction transducer 204 and an audio speaker 206 in another embodiment of the present invention. Providing an open ear audio solution with privacy in audio is a difficult problem. This is especially more challenging with eyewear frames where the temple arms are away from the ear canal 208. Audio firing from the temple towards the ear canal leaks outside and does not provide full private audio. Audio waves at higher frequency are more directional while the audio at lower frequencies are less directional. The low frequency audio, such as the bass frequency, works better using bone-conduction technology. The high frequency audio works better with small speakers. This embodiment takes advantage of these audio characteristics to use a combination of a bone-conduction transducer 204 and the audio speaker 206 in an eyewear temple arm 142. This embodiment splits the audio component into lower frequency and higher frequency using an audio crossover circuit. The low frequency component is sent to the bone conduction transducer while the high frequency component is sent to the audio speaker. The bone-conduction transducer is placed behind the ear 150 on the frame temple arm 142, contacting the skull bone behind the ear. With this placement of the bone-conduction transducer 204, the low frequency component of the audio reaches the ear through bone conduction, with minimal leakage outside. The high frequency component is fed to the audio speaker 206 that is designed to fire directional audio. This high frequency audio component with its inherent directional nature reaches the ear canal hole with minimal leak. The inner ear gets both low and high frequencies at high audio quality with minimal external leak.

Figure 12:
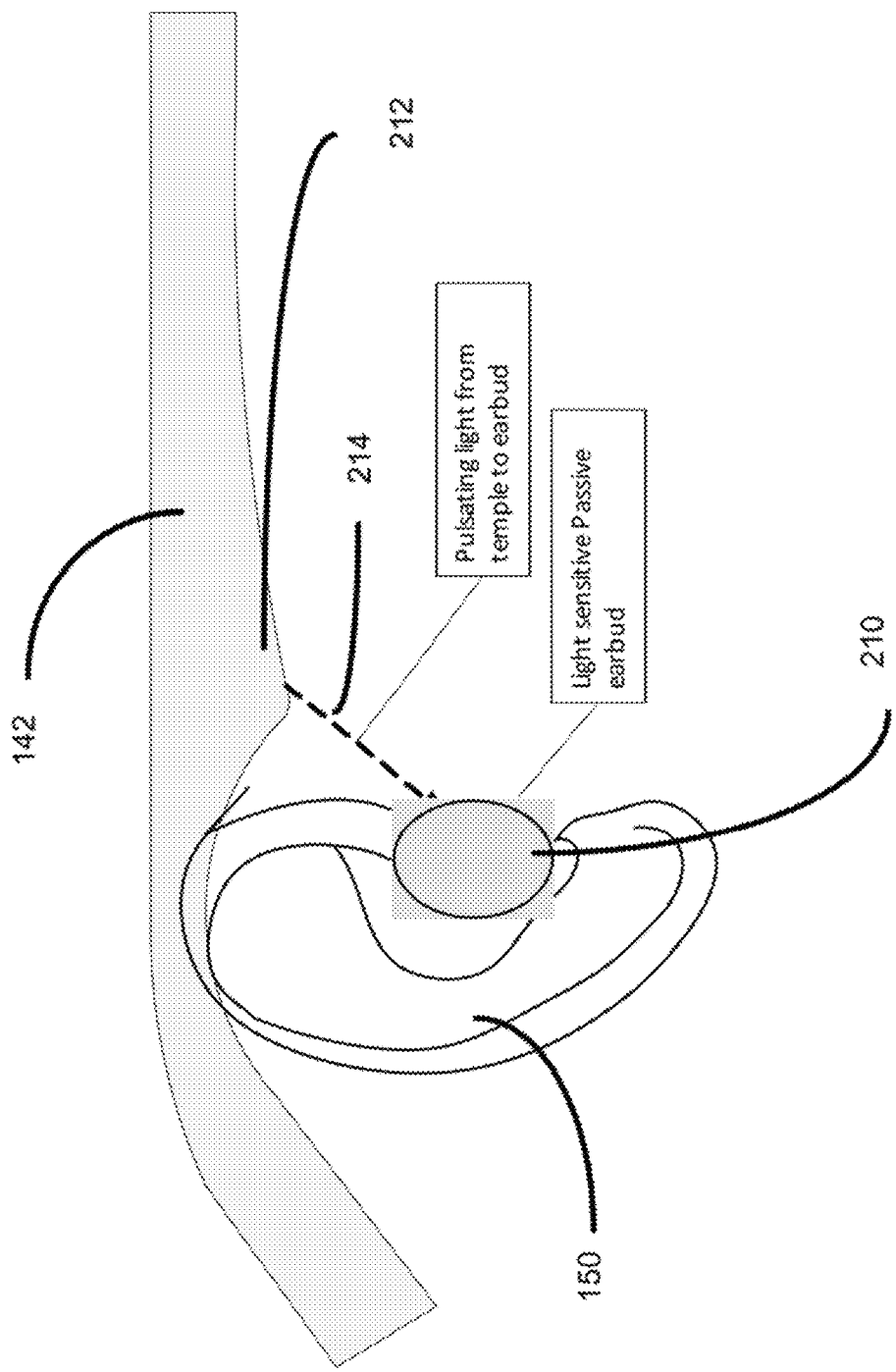
FIG. 12 is a side view of a graphene light pulse based micro audio earbuds in another embodiment of the present invention.

FIG. 12 is a side view of a graphene material light pulse based micro audio earbuds in another embodiment of the present invention, Graphene is a Nano-tube material that has several applications including being utilized as a speaker membrane. A type of light sensitive graphene vibrates with pulsating light beam when shined on it. This allows the speaker to create high quality audio with remote light pulses. In this embodiment, small passive light sensitive graphene earbuds 210 are positioned on the user's ear 150. These earbuds 210 are tiny devices without any electronics or battery. A light beam generator 212 positioned on the temple arm 142 would be used to direct a light beam 214 toward the earbud. The eyewear temple arm transmits the audio to the earbud with light pulses. When done listening to the audio, the user may remove the earbuds from the ear and may dock them in the temple arms.

Currently, voice assistance can recognize users' voice commands and have become pervasive for smart devices. In one embodiment of the present invention, the voice assistant feature is integrated in the eyewear 102 of the present invention. The user may invoke the voice assistant by a touch or with a wake word. The user's request is recorded with the mic and transmitted to the cloud. The response from the voice assistant from the cloud is played in the open ear speaker. This solution provides an always-on voice assistance to the eyewear user. Additionally, any text information received from the server or connected phone may be read to the user using text-to-speech conversion and played via audio in an open ear mode. Any information such as notification is also read to the user without the user reaching for the user's phone.

In another embodiment, a built-in accelerometer (not shown) of the eyewear 102 in the present invention may be utilized to provide information, such as fitness information (e.g., steps walked) to the user. In addition, the accelerometer data can be used to detect head gestures and to take user defined action. During an incoming call, the user can tilt the user's head up for few seconds and answer the call. The user may tilt the users head down for a few seconds to mute or reject a call. A multi-head shake gesture may be used to trigger a camera selfie or switch music to another song on the connected mobile phone. The accelerometer data also may be used to detect a fall by the user. With the aging population, a fall is a major concern for older people. Typical older person also wears eyewear glasses. The motion data from an accelerometer may be used to detect fall. The fast acceleration of the falling person's head towards the ground may help in this detection. The final orientation of the eyewear, which is provided by the accelerometer, after the fall can be used to confirm the fall. A normal user will have his head up and eyes facing forward, During the fall, this position is out of normal and movement also will be accelerated. By using a combination of head position before and after a fall and an accelerated movement, a fall detection is detected.

In another embodiment, the present invention provides heartrate detection and oximetry by using detection sensors integrated into the eyewear 102. The sensors may be placed either in the back-area of the temple arm behind the user's earlobe or in the front-area of the temple touching the user's forehead temple. The back-area around the earlobe provides better oximetry reading. The front-area provides better heartrate readings from the user's forehead temple. A light emitting diode (LED) may be fired toward the user's skin and the reflections from the veins of the underlying tissue detected for use by the heartrate sensor. The heartrate data may be further interpreted to detect the user's breathing rate. The breathing rate also may be used as a fitness rep counter when breathing is synchronized with a fitness routine.

In another embodiment, a wireless mesh network may be utilized with the present invention. Occupational glass, such as safety glass, is often used in work environments, such as construction sites, where users typically need to communicate with each other. Normally these kinds of users use safety glasses and bulky walkie-talkie units in this setting. In this embodiment, the eyewear is designed to replace the safety glasses and walkie-talkie units of such users by embedding low power and light eyewear temple arms using wireless mesh network. A low power short range wireless technology, such as Bluetooth, may be used for wireless communication. A mesh network typically is light and power efficient but comes at the cost of shorter wireless range. By communicating with a set of devices and hopping the signals from device to the next device, the wireless range is extended to cover longer distances. A mesh network is established between all the users' eyewear and a set of distributed access points. When one user broadcasts a message, the message is hopped from user to user or user to access points till it reaches all the end users. While each eyewear frame may have small and efficient short wireless range, hopping of data allows users to communicate over long distances. The user may broadcast a message to all or to a group or single person. Only the users to which sender intends to broadcast, pick up the audio packet and receive the audio.

The present invention may also utilize modular smart devices in the temple arms. The eyewear 102 of the present invention is designed so that all the electronics, battery and smartness is embedded in the frame temple arms. Both right and left temple arms may be independent units, either operating independently or communicating with each other. These smart temple arms are preferably made to be interchangeable with the frame fronts either with mechanical snaps or with magnetic snap connectors. The user then has the flexibility of switching the temple arms having different smart features and front rims of different styles. The smart temple arms on each side may communicate with each other wirelessly with a dummy front rim or communicate with wires built into the front. Different smart featured temple arms such as fitness temple arms, audio temple arms, hearing aid temple arms and camera temple arms can be designed for user flexibility and modular design.

Figures 13A, 13B, 13C:
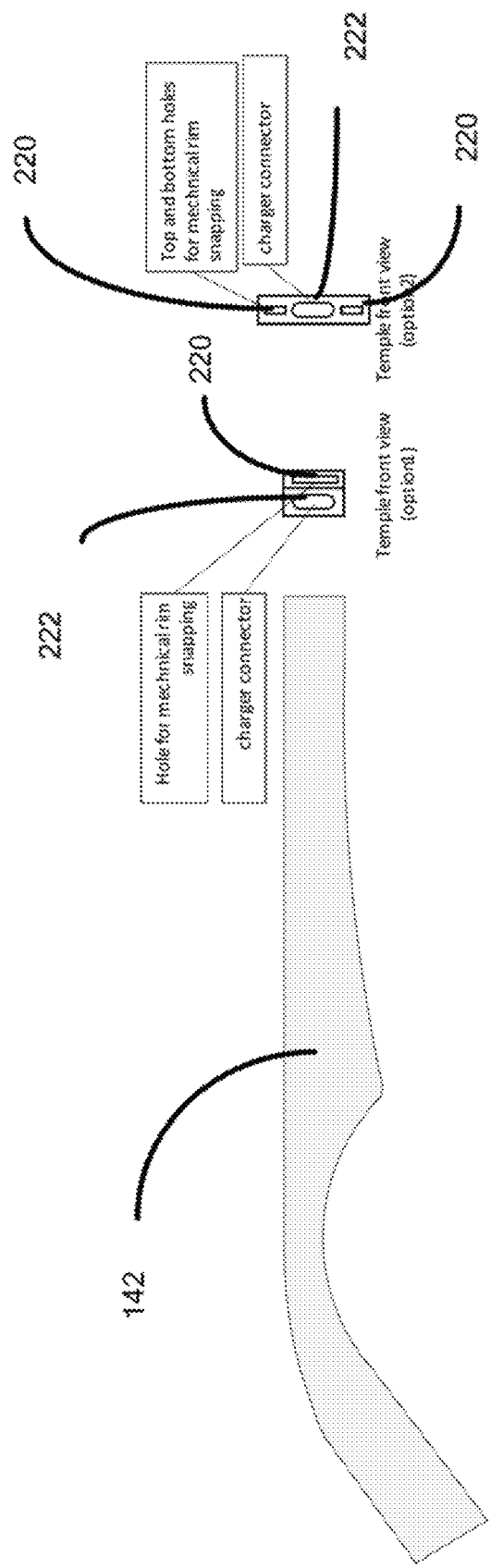
FIG. 13A illustrates a side view of the temple arm.
FIG. 13B illustrates a first configuration of the mechanical connector with a charging connector.
FIG. 13C illustrates a second configuration of two mechanical connectors with the charging connector.

In one embodiment, the temple arms 142 and 144 may have mechanical connectors 220 and a charging connector 222. FIG. 13A illustrates a side view of the temple arm 142. FIG. 13B illustrates a first configuration of the mechanical connector 220 with a charging connector 222. FIG. 13C illustrates a second configuration of two mechanical connectors 220 with the charging connector. The eyewear 102 of the present invention require electronic components to be placed cleverly in the temple arm area so that the frame does not look bulky. This placement is especially critical for a charger connector. Typical charger connectors are bulkier, and they are also required to be on the surface of the product for a charger cable to mate. In one embodiment of the present invention, the USB or other charger connector is made part of the snap connector in the front tip. It is designed in such a way that it seals the connector when the temple arm is open in a wear position. It exposes the connector for charging when the temple arm is closed inwards. The design also provides mechanical snaps outside the connector area for the temple arm to mate with the front rim of the eyeglass frames. This design allows the temple arm to be interchangeable or fixed with screws with the front rim. FIG. 14A is a top view of the temple arm 142 in an open configuration with the front rim 132 of the eyewear 102. FIG. 14B is a front view of the temple arm 142 in a closed configuration relative to the front rim 132 of the eyewear. FIG. 14C is a top view of the temple arm 142 disconnected from the front rim 132 of the eyewear 102. The temple arm mates with a front rim hinge 230 which rotates relative to the front rim. This area is also used as charging connector. Temple is removable, foldable and useable for charging. Holes in the temple arm tip 232 provide a mechanical snap with rim pins 234. The charging connector is placed around these holes. A gasket 236 may be used to seal the charger connector.

In one embodiment, the eyewear may include a wireless charging coil in the temple arms. The coil may be an elongated shape, optimized to fit in the rectangular temple arms space. Wireless charging such as inductive charging is used, where temple arms are mated with a transmitter charger coil. In another embodiment, a radio frequency (RF) transmitter may be placed in front at a specified location. The eyewear then charges as the user is located near the specified location.

Figure 15:
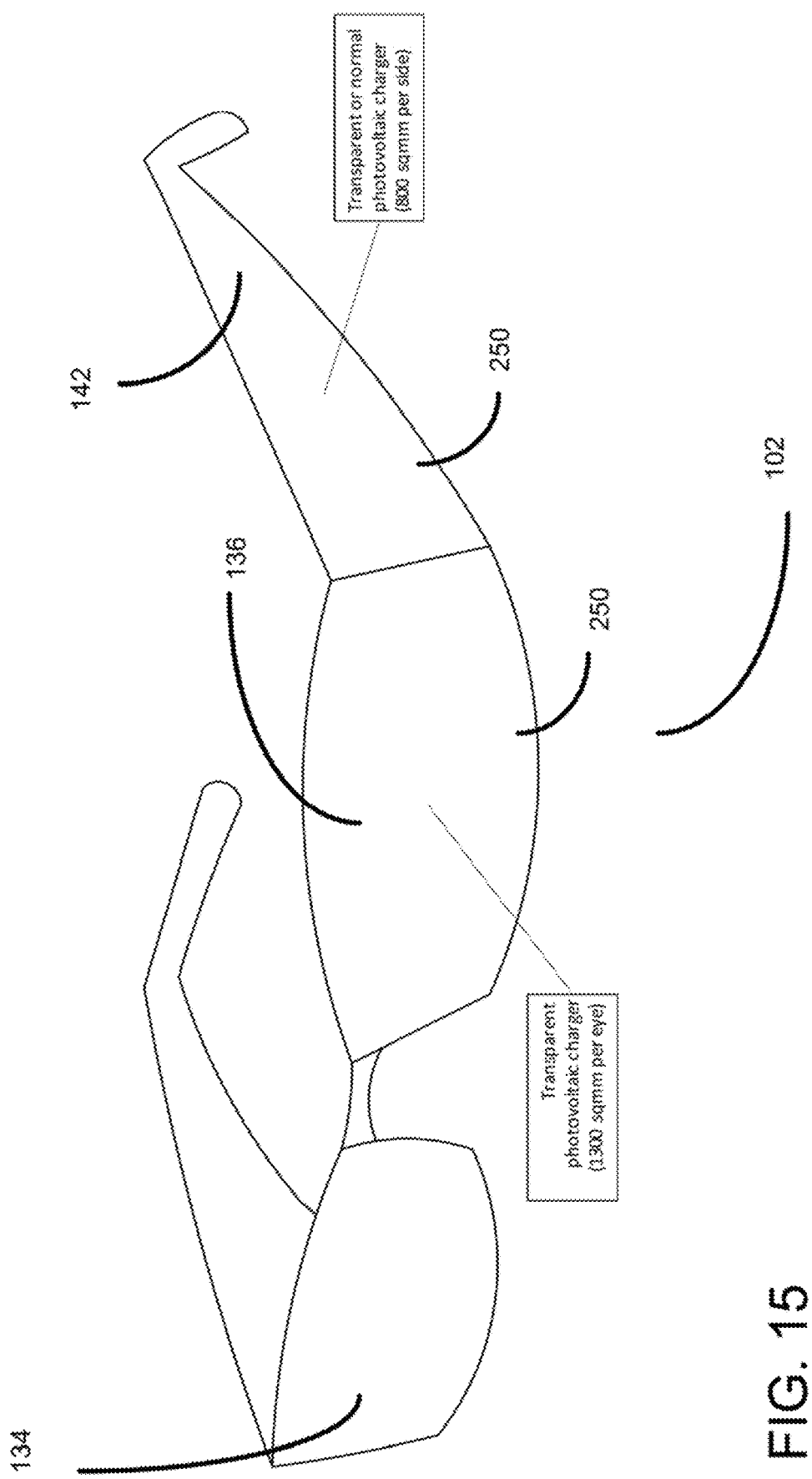
FIG. 15 is a front perspective view of the eyewear utilizing transparent photovoltaic cells in the temple arms and the lenses of the eyewear.

Transparent photovoltaic cells are disclosed in several patents. In U.S. Pat. No. 4,663,495, it discloses that photovoltaic cells may be transparent in selective spectral wavelengths such as the visible spectrum. U.S. Patent Application No. 2014/0130864 discloses the use of nanocrystal clusters embedded in a polymeric matrix to create transparent photocells, They typically work by passing visible light and converting power from the ultra-violet and infrared spectrum. In one embodiment, the smart eyewear of the present invention utilizes transparent and normal photovoltaic cells to charge the smart eyewear with ambient light. Using the transparent photocells, most of the surface of the eyewear can be covered to generate power from ambient light. FIG. 15 is a front perspective view of the eyewear 102 utilizing transparent photovoltaic cells 250 in the temple arms and the lenses of the eyewear. Each temple area can provide 8 square centimeters surface area and each eye lens area can provide 13 square centimeters surface area. In total area, in excess of 40 square centimeters is available in the eyewear frame to produce power from ambient light. A high efficiency photocell can generate about 100 uWatt power (100 uA at 1V or 30 uA at 3V). With about 40 square centimeters surface area, the eyewear can generate about 3.6 mWatt (about 1 mA at 3.3V). At this rate of power generation, a battery of 100 mAh capacity can be charged in about 100 hours or 6 days (without night charging). In a typical design, the smart eyewear has a battery capacity of 100 mAh and lasts for about 7 days in normal usage. With ambient light charging, the device can be designed to run forever without user manually charging. With solar charge efficiencies improving, this can further improve the eyewear function, An optional eyewear case charger may be provided to charge the device faster by shining bright light to the eyewear. This can charge more than 10 times faster, charging the eyewear in several hours.

Hearing aids are used to enhance the audio for hearing impaired. These devices enhance certain frequencies and filter noise from speech to make the speech more perceptible to the user. These devices use microphones to record audio, convert the audio to digital data, process the digital data with signal processing, convert digital audio to analog and finally play the audio in tiny in-ear speaker. The smart eyewear by design already has all the above components built in. It also has limited functions of signal processing needed for hearing aid. By enhancing the signal processing hardware of the smart eyewear, the eyewear can be made into an open ear hearing aid. Typical hearing aids are not liked by the user due to their visibility in the ear. The smart eyewear, in one embodiment, provides the hearing aid solution in an imperceptible fashion using the open ear speakers firing audio from eyewear frame directly towards the user's ear. All the audio enhancement functions of the hearing aid are provided by its internal signal processing. This solution provides enhanced experience to the user where the user's hearing aid functionality is transparent without any hint of hearing-aid looks. The only limitation of this embodiment is that the user hears both the external audio and enhanced audio at the same time with a small delay. The delay could be reduced to few milliseconds using pipelined audio processing hardware in the eyewear. Such a small delay between external and enhanced audio would not be recognizable by the user. Thus, in this embodiment, the user who has hearing impairment gets both eyesight and hearing enhanced from this eyewear.

In another embodiment, the eyewear in the present invention may include an auto remote key integrated into the eyewear. Passive entry car remote keyless entry systems are widely used for automobile access. The user carries a key fob to gain entry into the user's car. These systems use power from its battery and sometimes passive power from a car radio to communicate with the automobile to gain access. In one embodiment, the eyewear integrates the car keyless entry system hardware in the eyewear frames or optionally in a smart wrist band. The keyless entry systems use many common components that are used in smart eyewear and wrist band. The battery, power control, microcontroller and radio are common hardware components used both in keyless fob and smart wearables. Although the radio frequency and antenna may be different, the rest of the components may be shared between the smart wearables and keyless entry system. The user does not need to carry a car key fob for access to the user's car. The user of the present invention, i.e., wearing the eyewear or wearing a smart wrist band may gain access to the user's car transparently by just walking to the car. The touch and buttons on the smart wearable device provide additional controls to open the car or start the car engine. The user may also use gestures such as hand movement with eyewear or hand twist with a band to open car door or trunk.

The present invention may also provide other advanced functionalities. The present invention may utilize modular temple arms that may have many additional functions built into them with various combinations. The mix of smart features and modular nature of the temple arms allows the user the option of temple arms with the user's desired features. One such feature is a language translator. The user of the eyewear 102 may hear a language translated to the users native language. The audio recorded in the microphone is transferred to a connected mobile phone. The phone converts the audio to text using speech-to text. It further converts the text to a user's native language. Finally, the phone plays the converted native language text using text-to-speech wirelessly using the audio speakers on the smart eyewear. In another embodiment of the present invention, the eyewear may be used as a voice memo note taker. The user may use a pre-defined touch shortcut on the smart eyewear triggering memo recording. The recorded audio is stored as direct audio or converted to text using speech-to-text. In still another embodiment, the eyewear may include a functionality for measuring the user's body temperature. The eyewear frames provide an ideal location to take the user's body temperature. The body temperature is most accurate in the forehead temple area of the user. An infrared sensor may be placed on the eyewear temples facing towards the user's forehead temple. The measured temperature is recorded in the eyewear and connected phone or cloud.

The eyewear may also include a camera function. An optional built in camera on the frame can provide image or video capture to the user. This sensor can also act as an input to take actions. The camera input can be used to detect what the user is writing with optical character recognition (OCR). In the OCR mode, the user may write commands for the smart glasses to act. A side camera may be provided to detect a vehicle coming into blind spot during driving and warn the user with an LED indication. This may be useful while driving a car or a two-wheeler vehicle. When a user is waiting at the traffic signal light, the user must keep watching for the light change. This function can be automated with the camera located on the glasses. The camera detects the change from red to green light and indicate the change to the user with a buzzer or other indicator.

In still another embodiment of the present invention, the eyewear may include gradient based glare blocking eyeglasses. U.S. Pat. No. 7,651,220 to Pattikonda discloses dynamic electronic darkening of transparent medium which is used to darken/block the glare areas of the user's view, U.S. Pat. No. 7,651,220 is hereby incorporated by reference. The technology discussed in U.S. Pat. No. 7,651,220 for blocking the glare using a transparent display is enhanced with additional functionality of making the view more uniform. This is achieved with transparent display such as LCD. The pixels corresponding to the bright areas of the view are darkened while the pixels corresponding to dark areas are made fully transparent. This makes the image viewed by the user more uniform. In the present invention, this technology is used by the eyewear where the image is captured by the eyewear camera and analyzed through histogram. The technique utilizing histogram equalization is used to compensate for bright and dark areas. Once the compensation values are computed, the transparent display is activated with selective darkening. The result of this transparent display is similar to shaded sunglasses, where shading is controlled dynamically based on the field of view. FIG. 16A illustrates a front view of glasses 300 having clear lenses 302. As illustrated, no glare blocking technique is utilized. FIG. 16B illustrates a front view of glasses 310 utilizing gradient block 312 on the lenses 314. As illustrated, a bright top view is illustrated and where the gradient block 312 darkens around the bright top view. FIG. 16C is a front view the glasses 310 of FIG. 16B using spot sun block 320 to block glare from the sun. In addition, FIG. 16C also illustrates the gradient block 312 on the lenses 314.

The present invention provides may features currently unavailable in existing glasses. The present invention provides eyewear that includes advanced audio functions as well as various other functionalities.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. Eyewear comprising:
a frame having a first temple arm and a second temple arm;
wherein the frame has a front rim retaining a first lens and a second lens;
an open ear speaker for firing directional audio to an ear of a user, thereby providing semi-private audio to the user;
wherein the speaker is a side firing speaker producing directional audio and includes back volume, front volume and an audio slit opening.

2. The eyewear according to claim 1 wherein the eyewear includes a wireless connection module for connecting to another device or network.

3. The eyewear according to claim 1 wherein the speaker is movable toward an ear of the user by rotation or a slide mechanism to provide private audio to the user.

4. The eyewear according to claim 3 wherein the speaker includes a flexible tube for position toward the ear of the user.

5. The eyewear according to claim 1 wherein the speaker is configured to allow a hand of the user to cup the ear of the user to provide private calling for the user.

6. The eyewear according to claim 1 wherein the speaker includes a diaphragm configured to conform to a shape of one of the temple arms and the speaker is an odd-shaped planar speaker.

7. The eyewear according to claim 1 further comprising a passive light sensitive earbud configured for placement in an ear of the user and wherein pulsating light emitted from one of the temple arms provides audio to the user via the earbud.

8. The eyewear according to claim 1 wherein the speaker includes a combination of a directional audio speaker for higher frequencies and a bone conduction transducer for lower frequencies, the combination providing privacy calling to the user.

9. The eyewear according to claim 1 further comprising a microphone;
wherein the microphone and speaker provide voice assistant, music and phone call functionality to a user.

10. The eyewear according to claim 1 wherein the eyewear is connected to a mobile phone and converts received text to speech for the user.

11. The eyewear according to claim 1 wherein the eyewear further comprises a sensor for providing fitness information of the user.

12. The eyewear according to claim 1 further comprises a sensor for determining a heartrate of the user.

13. The eyewear according to claim 1 further comprising an accelerometer for detecting movement and tilt of a head of the user, the detection of the movement and tilt of the head of the use providing control inputs for a connected mobile phone.

14. The eyewear according to claim 1 wherein the first and second temple arms are simultaneously rechargeable.

15. The eyewear according to claim 1 wherein the eyewear is recharged wirelessly using a long-range power charger.

16. The eyewear according to claim 1 wherein the eyewear is recharged by affixing transparent photovoltaic cells on the first and second lens and a portion of the first and second temple arms, the photovoltaic cells recharging the eyewear with ambient light.

17. The eyewear according to claim 1 further comprising a communication device to communicate with another communication device of another user via a wireless mesh network by hopping signals within a group of distributed devices.

18. The eyewear according to claim 1 wherein the eyewear includes a wireless key fob function for accessing a car of the user.

19. The eyewear according to claim 1 wherein the eyewear includes a hearing aid functionality for use by the user to amplify or rectify sound.

20. The eyewear according to claim 1 wherein the eyewear includes a language translation function.

21. The eyewear according to claim 1 wherein the eyewear includes a mechanism for measuring a body temperature of the user, the mechanism using an infrared sensor facing a temple of the user.

22. The eyewear according to claim 1 further comprising an accelerometer for detecting a fall of the user.

23. Eyewear comprising:
a frame having a first temple arm and a second temple arm;
wherein the first and second temple arms are each independent and provide modular functionalities for the eyewear;
wherein the frame has a front rim retaining a first lens and a second lens;
wherein the first and second temple arms are detachable from the front rim using snap connectors for quick detachment and reattachment of the first and second temple arms from the front rim.

24. The eyewear according to claim 23 wherein each temple arm includes a charging connector providing an electronic and mechanical connection with the eyewear.

25. The eyewear according to claim 23 wherein the first temple arm communicates with the second temple area wirelessly or via a wire connecting the first and second temple arms.

26. The eyewear according to claim 23 wherein the eyewear includes a camera or sensor for detecting a signal light color change and indicator to the user of the change of signal light color.

* * * * *